United States Patent [19]

Ewing

[11] Patent Number: 4,823,778

[45] Date of Patent: Apr. 25, 1989

[54] FACIAL EXERCISE METHOD

[76] Inventor: Carol A. Ewing, 7011 Biscayne, Milford, Mich. 48042

[21] Appl. No.: 724,282

[22] Filed: Apr. 17, 1985

[51] Int. Cl.$^4$ ............... A61F 5/08; A63B 21/12
[52] U.S. Cl. ........................ 128/76 B; 272/119; 272/95
[58] Field of Search ............ 272/94, 95, 119, 93; 128/76 R, 76 B, 163; 15/104 A; 428/343, 344, 40; 446/85

[56] References Cited

U.S. PATENT DOCUMENTS

| | | | |
|---|---|---|---|
| 2,001,862 | 5/1935 | Battey | 128/163 |
| 2,401,842 | 6/1946 | Slater | 15/104 A |
| 2,854,682 | 10/1958 | Berezny | 15/104 A |
| 4,189,141 | 2/1980 | Rooney | 272/95 |

FOREIGN PATENT DOCUMENTS 916745 12/1946 France ............... 128/76 B

OTHER PUBLICATIONS

Face-Lifting by Exercise, Santa Maria Runge, published 1980.
Face Saving Exercises, Craig, published 1970.
The 15-Minute-A-Day Natural Face Lift, M. J. Saffon, published 1979.

*Primary Examiner*—Richard J. Apley
*Assistant Examiner*—J. Welsh
*Attorney, Agent, or Firm*—Reising, Ethington, Barnard, Perry & Milton

[57] ABSTRACT

An exercise method is disclosed for improving the tone of the facial muscles and thereby removing or reducing wrinkles in the overlying skin. A facial muscle underlying a region of skin to be tightened is selected for exercise. The primary stiffener is applied to the surface of the skin over the selected muscle and secondary stiffeners are applied to other regions of the skin which would be creased by contraction of the selected muscle. An exercise weight is attached to the primary stiffener at a location over the selected muscle. The selected muscle is contracted and released repeatedly to lift and lower the weight a predetermined number of times.

9 Claims, 1 Drawing Sheet

FACIAL EXERCISE METHOD

FIELD OF THE INVENTION

This invention relates to a method for preventing or removing wrinkles from the facial skin; more particularly, it relates to a method of exercise for improving the tonus of the facial muscles and thereby tightening the facial skin.

BACKGROUND OF THE INVENTION

It is well known that in the aging process of the human body, the facial skin tends to droop and become flabby with the development of wrinkles in the skin and hollowness in certain facial regions. Many persons desire to retain or restore the firmness and evenness of the facial contour which is associated with youth. Surgical face-lifting has long been a common practice and is effective to tighten the facial skin. However, as a result of tightening the skin by this technique, the skin is caused to support the underlying muscle. If it is lacking in tone, it is lengthened and droopy and is the major contributing cause of wrinkled and droopy facial skin. Since the skin is not adapted to support the underlying muscles, this creates an even stronger tendency for the skin to droop and wrinkle. Consequently, the surgical face-lift provides a temporarily tightened facial skin with the appearance of a lift of the facial contour; however, it also starts the process of drooping and wrinkling over again.

It is understood that the contour of the face is determined by the condition of the muscles beneath the skin. When the muscles underlying the facial skin are strong and have good tone, the skin is tight and smooth and the face has a youthful appearance. However, as the facial muscles lose tone, by reason of aging or lack of proper exercise, the muscles elongate and droop or sag. This results in a change of facial contour with attendant wrinkles in the skin.

In the prior art, several techniques have been developed for the purpose of improving muscle tone with the purpose of preventing or removing wrinkles in the skin. The known prior art is as follows.

The Rooney Pat. No. 4,189,141 granted Feb. 19, 1980 discloses a facial exercise mask which is made of an elastic two-way stretch cloth material. Weights of metal are enclosed in pockets in the mask at selected positions such as the brow, temple and cheek. With the mask in place, the wearer performs prescribed muscle exercises.

The Robins U.S. Pat. No. 3,386,732 granted June 4, 1968 describes a facial exercise device comprising a mouthpiece which is inserted between the lip and the gum area to serve as a reaction member. Selected muscles are exercised by tensioning and relaxing against the mouthpiece. The Robins U.S. Pat. No. 3,507,493 granted July 29, 1968 discloses a device for muscle exercising which is applied to the forehead to provide a resilient resistance to movement of selected muscles.

In a publication by Runge, a method of isometric facial exercises is described to tighten elongated muscles and thereby produce a lift for the facial contour where the muscles have atrophied. See *Face-Lifting By Exercise*, Senta Maria Runge, Allegro Publishing Company, 1980. In this method of isometric facial exercise, a selected muscle is worked against a resistance which is applied at the point of muscle function, i.e. the point at which the muscle is attached to the skin. In the execution of the exercise, the entire face is to be relaxed and only the selected muscle is moved. For example, a set of exercises is described for lifting and firming the upper cheeks and for removing the furrows of the laugh lines. For this purpose, the muscles known as the quadratus, labii, superioris, and zygomaticus are selected for exercise. Each of these muscles extends from the area of the temples and the eye-ring muscles toward the nose and mouth. These upper cheek muscles are attached to the skin along a line which extends from the side of the nose to the corresponding side of the mouth, a line which is referred to as the laugh line which curves at a place called the smile line. Preliminary to the isometric exercises, the location of the individual muscles is marked with a suitable make-up pencil and the person practices moving each of the muscles independently and in combination. For the isometric exercise, the thumbs are placed inside the mouth under the laugh line and the points of action of the muscles are held by placing the forefingers along the laugh line and gripping the muscles between the thumb and fore finger. The laugh line is pulled downwardly slightly and held fixed as the point of resistance for the muscle movement. Then, the four muscles, for example, are contracted together as by forming a smile; the muscle contraction being executed in distinct steps from the relaxed state to complete contraction. Then, the muscles are returned by stepped movement to the starting position and the finger resistance is removed. This exercise is repeated a predetermined number of times. Similarly, isometric exercises are described for the upper cheek muscles individually or in combination.

Facial exercises which are executed without imposing special resistance to muscle movement, except for gravity, are described in a book by Craig. *Face Saving Exercises*, Craig, Random House, 1970. One or more exercises are provided for each different facial area such as the forehead—scalp, eyelids, nose, cheeks, upper lip and mouth, chin and jaw line, and underchin and throat. In the exercises for removing forehead wrinkles and to lift drooping eyebrows, an exercise is described for the frontalis muscle and for the occipitalis. The frontalis muscle extends upwardly from the eyebrows to join with the tendinous fibers of the scalp and the occipitalis muscle extends from the rear of the scalp to the base of the skull. The exercise is executed by the person lying face up on a bed with the head hanging over the edge for the purpose of applying the force of gravity in the desired direction. The exercise comprises contracting the frontalis muscle to raise the eyebrows as high as possible then returning the eyebrows to the normal position and repeating the exercise a prescribed number of time.

In *Natural Face Lift* by Saffon, Warner Books, 1979, facial exercises are described for removing wrinkles by massaging the muscles with the hands. For example, to develop the frontalis muscle and smooth the forehead, the balls of both hands are used to massage the forehead by moving the hands in opposite directions to move the muscle while stretching the skin as little as possible. After completing this exercise and similar exercises for the forehead, tape is applied to the forehead. The tape acts as a remainder not to gesture or scowl with the forehead and is said to prevent additional lines from forming above the eyebrows. The recommended tape is microporous surgical tape of three-quarter inch width. Three strips of overlapping tape are applied to the forehead and extend from temple-to-temple and a fourth overlapping tape extends between the eyebrows.

A general object of this invention is to provide an improved method of exercising the facial muscles.

SUMMARY OF THE INVENTION

In accordance with this invention, a method of exercising facial muscles is provided which is effective to improve the tone of the muscles and to eliminate wrinkles in the overlying facial skin. The exercise method can be executed with proficiency after proper instruction and with simple inexpensive equipment. Favorable results are achieved after regular practice of a prescribed program over a relatively short period of time.

According to this invention, a facial muscle underlying a region of skin to be tightened is selected for exercise. A primary stiffener is applied to the surface of the skin over the selected muscle and a secondary stiffener is applied to other regions of the skin which would be creased by contraction of the selected muscle. An exercise weight of selected size and weight is attached to the primary stiffener at the location over the selected muscle. The selected muscle is contracted and released repeatedly to lift and lower the weight a predetermined number of times. The exercise is executed periodically whereby the selected muscle achieves good tone and is shortened so that the skin overlying it is tightened to eliminate wrinkles.

A more complete understanding of this invention may be obtained from the detailed description that follows taken with the accompanying drawings.

BEST MODE FOR CARRYING OUT THE INVENTION

An illustrative embodiment of the invention is set forth in the following description and the accompanying drawings. It will be appreciated as the description proceeds, that the invention may be practiced in other embodiments and for the purpose of realizing results other than prevention and removal of wrinkles of the facial skin.

GENERAL DESCRIPTION

The exercise method of this invention is adapted to develop good tone in a selected muscle underlying a facial area which exhibits wrinkled or sagging skin or is subject to wrinkling or sagging with the passage of time. In the aging process, muscles tend to lose their tone and tend to elongate or stretch with the result that the attached facial skin is caused sag and form wrinkles. When the frontalis muscles contract, for example, the skin of the forehead is temporarily formed in horizontal creases. When the contraction is released, if the frontalis muscles are in good tone they will relax and lengthen fully while still maintaining a slightly tonus state, i.e. the normal state of slight but continuous contraction in a muscle as opposed to total relaxation. Thus, in the tonus state the overlying skin is sufficiently tight to be smooth and wrinkle free. The desired tonus state of the selected facial muscles is achieved by the exercise method of the invention to be described presently.

Before doing the exercises, certain preparatory steps should be taken to insure comfort and to protect the skin. First, a moisturizer should be applied to the skin to keep it from feeling dry or tight. Second, the lips should be lubricated with a lip gloss to prevent feeling of dryness or stretching. Third, a protective or stiffening tape is applied at selected locations to prevent etching lines deeper into the face, as will be described below.

PROTECTIVE TAPING

Figure 1:
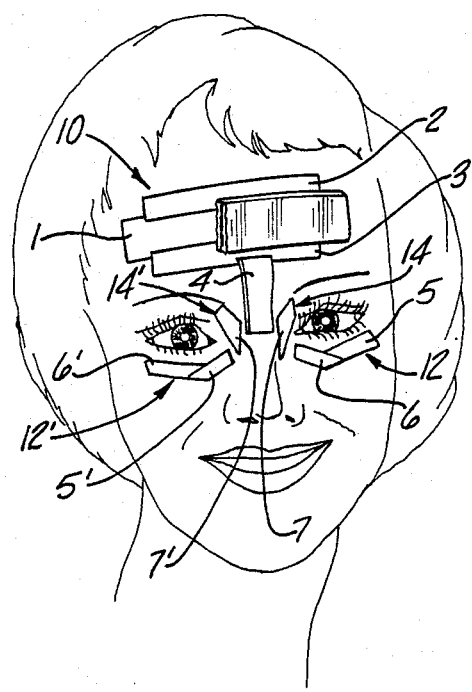
FIG. 1 shows a person's face with stiffener tape and a forehead wide band exercise weight applied in accordance with this invention.

Certain areas of the face are susceptible to creasing during exercise and unless proper precautions are taken, the lines in such areas will be etched deeper as a result of the exercise. Protective taping is to be used with all of the facial exercises. The areas to be protected are the forehead, under the eyes and the sides of the top of the nose. Tape applied to the skin acts as a stiffener of the selected areas and changes the crease point of the skin so that the selected muscle can be exercised without creasing in the normal wrinkle lines. A suitable tape is a conventional pressure sensitive first aid tape of sturdy and lightweight structure, preferably hypo-allergenic. The application of the stiffening tape will be described with reference to FIG. 1. A forehead stiffening tape 10 is first applied using plural strips of tape. First, a tape strip 1 long enough to extend across the entire forehead is applied to the center of the forehead. Next, a tape strip 2 is placed above strip 1 and slightly overlaps it. A third tape strip 3 is applied below strip 1 and also slightly overlaps it. Next, the short tape strip 4 is applied vertically between the eyes with the upper end overlapping tape strip 3. The forehead stiffening tape 10 should cover substantially the entire forehead and typically, a tape width of one-half inch will be satisfactory for most persons. Persons having an unusually wide forehead may need to use three-quarter inch or one inch tape for the forehead stiffening tape. A set of under-eye stiffening tapes 12 and 12' are applied as follows. Stiffening tape 12' is a mirror image of tape 12 with corresponding parts having the same reference character in the drawings with a prime symbol added. A tape strip 5 is applied below the outer portion of the lower eyelid on the crease line. Next, a tape strip 6 is applied diagonally under the inner corner of the eye with the end slightly overlapping the end of tape strip 5. Note that the two tape strips form a V-shape approximately centered under the eye. The under-eye stiffener tape 12 is should be placed on the junction of the lower eyelid and cheek so that it does not interfere with the closing of the eye. A pair of nose stiffener tapes 14 and 14' are applied on opposite sides of the top of the nose. These stiffener tapes comprise tape strips 7 and 7', respectively, and are located on the areas where "crinkle" lines form. If the person does not have such lines, this stiffening tape is not required but otherwise should be used.

EXERCISE WEIGHTS

Figure 2:
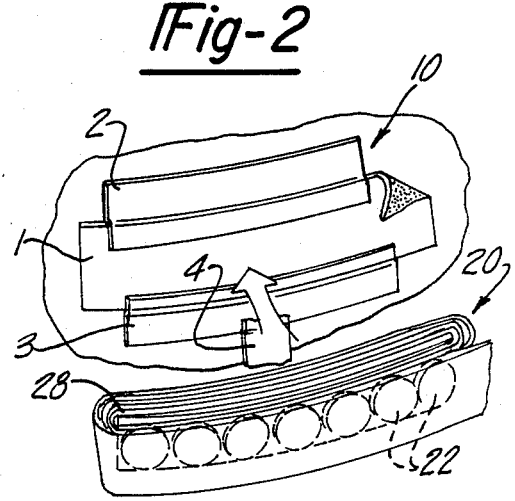
FIG. 2 shows a portion of the stiffener tape and the forehead weight in greater detail.
Figure 3:
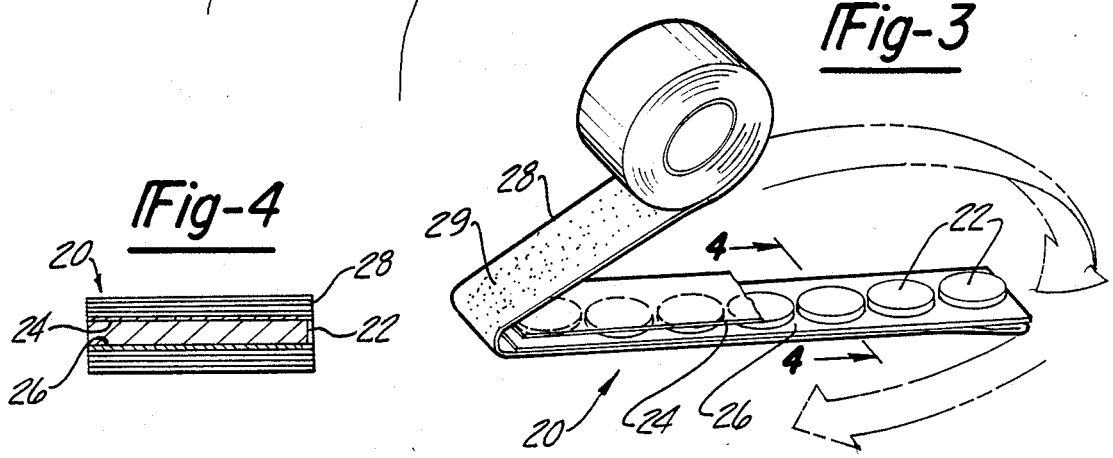
FIG. 3 shows the construction of the forehead weight.
Figure 4:
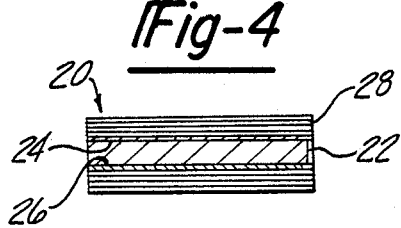
FIG. 4 is a view taken on lines 4—4 of FIG. 3.
Figure 5:
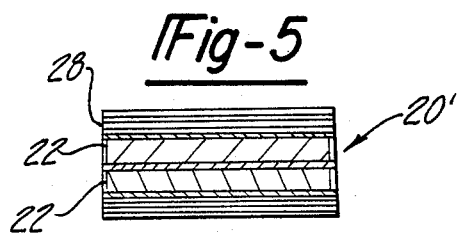
FIG. 5 shows a modification of the forehead weight.

Special exercise weights are used in conjunction with the exercise method of this invention. The use of the weights will be described subsequently; the weights themselves will now be described with reference to the drawings. A wide band or forehead weight 20 is shown in FIGS. 2, 3 and 4. It is of strip-shape and comprises a set of seven weight elements in the form of metal disks 22 disposed in a row. The disks 22 are about the size and weight of a copper penny. The disks are sandwiched between a pair of thin cardboard plates 24 and 26 and suitably held in place with an adhesive. The cardboard plates 24 and 26 are wrapped end-to-end with several layers of pressure sensitive adhesive tape 28. The tape and cardboard plates are preferably about three-quarter inches wide. The tape is suitably a thin paper tape and is hypo-allergenic with adhesive on one side. It is wound with the adhesive surface 29 on the outside and about eight or ten layers are applied. In the drawings, the thickness of the tape is exaggerated for clarity and, in practice, the thickness of the forehead weight 20 is relatively thinner than shown. A set of graduated forehead weights are provided. A first degree forehead weight 20 is as shown in FIGS. 2, 3 and 4 and comprises a single layer of weight elements or disks 22. A second degree forehead weight, shown in cross-section in FIG. 5, comprises a double layer of disks 22 but otherwise is of the same construction. A third degree forehead weight comprises a triple layer of disks 22.

Figure 6:
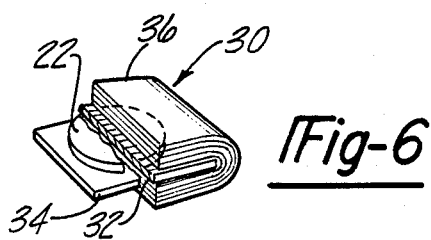
FIG. 6 shows the construction of a narrow band weight.

A set of narrow band or cheek weights is also provided and, an example cheek weight 30 is shown in FIG. 6. The construction is similar to that of the forehead weight 20. The cheek weight 30 comprises a single disk 22 sandwiched between cardboard plates 32 and 34 and provided with a wrapping of adhesive tape 36 in several layers with the adhesive side out. The cheek weight shown in FIG. 6 is a first degree weight, i.e. it contains a single disk 22. Second degree and third degree cheek weights are also provided and comprise two disks and three disks, respectively, in a stacked arrangement.

The exercise weights are designed to be attached to selected areas of the facial skin to offer resistance necessary to strengthen the underlying muscles. The graduated weights are used in sequence in the exercise program and are suitably color coded to signify first degree, second degree and third degree. The weights are atatched in the selected area by pressing the adhesive surface thereof into engagement with the stiffening tape. The exercise weights are not to be attached to the skin itself. The weights should be detached with care to avoid stretching the underlying skin, by pressing down on the stiffening tape. A fresh adhesive surface of the exercise weight is to be applied against the stiffener tape each time the weight is used. For this purpose, the outer layer on one side of the weight is peeled off after it has been used to expose the fresh underlying layer. When the layers of tape are used up, new layers may be applied for continued use of the weight.

After a session of facial exercise, steps should be taken to care for the skin. The stiffening tape should be removed gently to avoid stretching the skin and the adhesive residue should be removed by baby oil. After blotting off the excess baby oil the skin should be refreshed by wiping it with a cotton ball saturated with a gentle toner. For the eyes, a cotton tip stick saturated with a non-oily eye makeup remover may be used. Next, a cotton ball saturated with water should be used to remove the residue and to rehydrate the skin. Finally, a moisturizer should be applied generously over the freshly cleansed areas.

EXERCISE METHOD

The exercise method of this invention is incorporated into a program of exercises. The overall exercise program is designed to reduce or eliminate wrinkles from the entire facial area. The exercise program is adapted for periodic execution, preferably daily, of the entire set of exercises. However, not all of the individual exercises need be included; a part of the exercise program, or even an individual exercise, may be selected to meet the particular needs of an individual.

The exercise program comprises the following set of exercises:

| | I. The Muscles Of The Forehead |
|---|---|
| | A. Occipitofrontalis |
| Exercise 1 | Warm-up Massage |
| Exercise 2 | Eye Squeeze and Eyebrow Lift |
| Exercise 3 | Eyebrows Lift and Lower (Weights) |
| Exercise 4 | Single Eyebrow Lift and Lower (Weights) |
| Exercise 5 | Outer Eyebrow Weight Lifts (Weights) |
| Exercise 6 | Inner Eyebrow Weight Lifts (Weights) |
| Exercise 7 | Eyebrows Lift and Lower "Double Time" (Weights) |
| | B. Corrugator Supercilii |
| Exercise 8 | Eyebrows Down and Out, Lift and Separate |
| | C. Procerus |
| Exercise 9 | Eyebrows Down to Nose and Stretch Up |
| | II. The Muscles Of The Eyes |
| | D. Orbicularis Oculi |
| Exercise 10 | Upper Eyelid Stretch |
| | E. Levator Palebrae Superioris |
| Exercise 11 | Top Lid Lowers Half Mast |
| Exercise 12 | Top Lid Lowers Advanced |
| | F. Lower Palpebral Portion - Oribucularis Oculi |
| Exercise 13 | Lower Eyelid Lifts |
| Exercise 14 | Lower Lid Lifters - Tilt Side-To-Side |
| Exercise 15 | Lower Lid Lift and Eye Roll - Look Up |
| Exercise 16 | Eyelid Resistors |
| | III. The Muscles Of The Upper Cheeks |
| | G. Levator Labii Superioris Aleque Nasi |
| Exercise 17 | Nose Wrinkle - Ups |
| | H. Levator Labii Superioris |
| Exercise 18 | Cheek Isometrics |
| Exercise 19 | Cheek Lifts with Weights (Weights) |
| | I. Zygomaticus Minor |
| Exercise 20 | Smiling Winks |
| | J. Zygomaticus Major |
| Exercise 21 | Mouth Corners Lift with "Ha-Ha's" |
| | IV. The Muscles Of The Nose |
| | K. Nasalis |
| Exercise 22 | Simple Nostril Flares |
| Exercise 23 | Complex Nostril Flares |
| | V. The Muscles Of Mastication |
| | L. Temporalis |
| Exercise 24 | Big Chews |
| | M. Masseter |
| Exercise 25 | Back Bite |
| Exercise 26 | Jaws in Fours |
| | N. Pterygoids |
| Exercise 27 | Lower Jaw Forward and Side-to-Side |
| Exercise 28 | Jaw Circles |
| | VI. The Muscles Of The Lower Cheek Area |
| | O. Risorius |

| | -continued |
|---|---|
| Exercise 29 | Straight Smile and Pull into a Pucker |
| | P. Buccinator |
| Exercise 30 | Cheek Isometrics |
| Exercise 31 | Advanced Cheek Contractions |
| Exercise 32 | Half Smile and Pull In |
| | Q. Levator Angeli Oris |
| Exercise 33 | Wide Smile to an "O" |
| | VII. The Muscles Of The Mouth |
| | R. Orbcularis Oris |
| Exercise 34 | Lip Presses |
| Exercise 35 | Top Lip Presses |
| Exercise 36 | Jaw Juts and Top Lip Forward |
| Exercise 37 | Upper Lip Squeeze |
| Exercise 38 | Lower Lip Squeeze |
| Exercise 39 | Clapping Lips |
| | VIII. The Muscles Of The Chin And Jawline |
| | S. Mentalis |
| Exercise 40 | Chin Raises |
| | T. Depressor Labii Inferioris |
| Exercise 41 | Lower Lip Down and Out |
| | U. Depressor Anguli Oris |
| Exercise 42 | Lower Lip - Pout and Pull Down |
| | V. Platysma |
| Exercise 43 | Lift Upper Lip Lower Lip Corners Down |
| | IX. The Muscles Of The Under-Chin, Throat And Neck |
| | W. Suprahyoids |
| Exercise 44 | Tongue Lifts |
| Exercise 45 | Tongue Side To Side (Metronome) |
| Exercise 46 | Kiss and Smile Down, Kiss and Smile Center |
| Exercise 47 | Head Returns Against Resistance |
| | X. Inverted Head (Hangover) Exercises |
| | X. Diagastric |
| Exercise 48 | Teeth Touches |
| | Y. Sternocleidomastoid |
| Exercise 49 | Head Raises |
| Exercise 50 | One Sided Head Raises |
| Exercise 51 | Lip Push-Ups |
| Exercise 52 | Eye Squeeze and Upper Lip Stretch |

In the exercise program set forth above, only the exercises of the muscles of the forehead and the exercises of the muscles of the upper cheeks are executed with the combined weight lifting and protective taping of this invention. The remaining exercises of the program are executed with protective taping but without weight lifting. Accordingly, only the exercises of the forehead muscles and the upper cheek muscles will be described in detail.

MUSCLES OF THE FOREHEAD The Occipitofrontalis Muscles

The occipitofrontalis muscles are made up of the frontalis muscle and the occipitalis muscle which are united by a broad tendinous sheet that covers the top of head. The frontalis is the forehead portion of the muscle and the right and left frontalis cover most of the area of the forehead. The occipital pair of muscles are located at the base of the skull. When the frontalis muscles contract, they shorten, pulling up the eyebrows and temporarily causing horizontal creases to form in the skin across the forehead. When both the frontalis and the occipitalis muscles contract, they move the scalp. Contracting the frontalis muscles is a common voluntary action and is done to raise the eyebrows in, for example, the expression of surprise. contracting the occipitalis muscles voluntarily is uncommon but is greatly facilitated with the help of the forehead weight.

Exercise 1 - Warm Up Massage

Purpose:

To stimulate and reopen the nerve channels from the brain to the individual muscles so that the muscles can be moved at will and to increase blood circulation to each muscle.

Preliminary Preparation:

The forehead stiffener tape 10, under-eye tapes 12 and 12' and, optionally, the nose stiffener tapes 14 and 14' are applied as described. (Protective taping is to be used with all of the exercises.)

Exercise Steps (1) With the fingers evenly spaced along the center of the forehead, apply gentle pressure and using horizontal strokes, massage across the forehead and eyebrows out past the temples into the hairline.

(2) Massage the muscle surrounding the eyes with a light stroking motion, using the pads of the middle fingers. Begin at the lower corners of the eyes, just below the eyebrows. Massage above the upper eyelids, circling out and down past the outer corners of the eyes.

(3) When the massaging action of step 2 reaches the lower outer corners of the eyes, look up slightly. Massage under the lower eyelids using a pat and press motion from the outer corners to the inner corners of the lower eyelids. Press gently and do not pull or stretch the skin.

(4) When the massaging action of step 3 reaches the inner corners of the lower eyelid, use a pat and press motion and continue to look up slightly.

EXERCISE 2 - EYE SQUEEZE AND EYEBROW LIFT

Purpose:

To fully contract and start to strengthen the muscles surrounding and including the upper and lower eyelids. Also, to warm-up the forehead muscles for the weight work that follows.

Exercise Steps (1) Squeeze the eyes shut tightly; allow the teeth to separate slightly and squeeze the eyes shut as tightly as possible. (This enables the "surrounding" eye muscles to be fully contracted and allows the cheek muscles to start working also.) Hold the squeeze for eight counts. (In all exercises, take about one second per count.) Note: The first time the squeeze is done, massage around the orbital portion of the orbicularis oris (circling from the inner/upper corners, out, around, down and under) to stimulate a harder contraction.

(2) Slowly release the squeeze (in a four count motion) and finish by firmly planting the upper teeth against the lower teeth. This insures that the cheek muscles have been fully released.)

(3) With the eyes still closed, lift the eyebrows and stretch the eyelid down over the closed eyes. (Think of trying to push down as hard as you can on your eyelashes.) Hold the stretch for eight counts. Note: The first time the stretch is done, use a pat/press motion from the inner to the outer palpebrals to stimulate a harder stretch.

(4) Slowly release the stretch, to a slow count of four, and lower the eyebrows back down to the normal position. Inhale and exhale as you consciously relax the eyelids.

(5) Repeat steps 1 through 4 four times.

EXERCISE 3 - EYEBROWS LIFT AND LOWER WITH WEIGHTS

Purpose:

To lift and tighten the frontalis muscles and to smooth the skin of the forehead.

Procedure and Preparation: The following steps should be executed first without attaching any weights for the purpose of warm-up and to develop the technique. Next, the forehead weight is attached to the forehead stiffening tape 10 in the middle of the forehead, as described.

Exercise Steps (1) Sitting up very straight and tall, look directly into a mirror. To a slow count of four, lift the eyebrows up as high as they will go.

(2) With a controlled movement to a count of four, slowly lower the eyebrows back to their normal position. (Note: The controlled lowering is the most important part of this exercise.) Repeat the raise and the lower slowly, working up to eight times in all.

(3) To a slow count of four, raise the eyebrows again.

(4) Slowly lower the eyebrows only half way down.

(5) From the half way position of step 4, raise the eyebrows again, lifting them even higher than before. Hold for four counts.

(6) Repeat steps 4 and 5, working up to four times in all.

(7) Return the eyebrows to their normal position and inhale and exhale to relax.

EXERCISE 3 - SINGLE EYEBROW LIFT AND LOWER WITH Weights

Purpose:

To strengthen each frontalis muscle individually and to restore or preserve symmetry of the eyebrows.

Preparation:

Attach the forehead weight as in Exercise 3.

Exercise Steps:

(1) Immobilize the left eyebrow by placing first and second fingers of one hand on its inner and outer corners. Press firmly to keep the eyebrow from moving.

(2) Now using the right eyebrow only, raise it up to a slow count of four.

(3) Lower the right eyebrow slowly to a count of four.

(4) Repeat steps 2 and 3 of four to six times on the right side.

(5) Repeat steps 1 through 4 for the other eye.

(6) If one eyebrow is lower than the other, repeat the exercise on the weak side several more times.

EXERCISE 5 - OUTER EYEBROW WEIGHT LIFTS

Purpose:

To strengthen the outer or lateral portion of the frontalis muscle, to lift the outer portion of the eyebrow and help to eliminate puffiness above the upper eyelid.

Preparation:

Attach the forehead weight as in Exercise 3.

Exercise Steps (1) Immobilize the inner corners of both eyebrows by placing the middle fingers firmly on them.

(2) Slowly raise the forehead weight to a count of four using the outer portion of the frontalis only.

(3) Slowly lower the weight and return the eyebrows to their normal position.

(4) Repeat steps 2 and 3 four times, each time trying to raise the outer corners of the eyebrows up a bit higher.

EXERCISE 6 - INNER EYEBROW WEIGHT LIFTS

Purpose:

To strengthen and tone the inner or medial portion of the frontalis. This will lift the inner corner of the eyebrows and help to eliminate any sagging between the brows or transverse lines on the bridge of the nose.

Preparation:

Attach the forehead weight as in Exercise 3.

Exercise Steps (1) Immobilize the outer corners of both eyebrows by placing the middle fingers on the arch of the eyebrows and the pointer fingers on the outer corners.

(2) With the outer corners immobilized, slowly raise the inner eyebrows to a slow count of two.

(3) Lower the inner eyebrows to their normal position to a slow count of two.

(4) Repeat steps 2 and 3 three or four times.

EXERCISE 7 - EYEBROWS LIFT AND LOWER "DOUBLETIME" WITH WEIGHTS

Purpose:

To help get in touch with and strengthen the occipital muscles in the back of the head as well as to strengthen and increase the muscle mass of the frontales.

Preparation:

Attach the forehead weight as in Exercise 3. Do not do this exercise unless the frontales muscles are well warmed up from doing several of the previous forehead exercises.

Exercise Steps (1) Sit up tall and tilt the head forward and look down at the lap.

(2) Holding the position of step 1, raise and lower the forehead weight quickly ten to twelve times. Try to keep the lowering motion controlled even though it is fast; do not just let the eyebrows and weights drop.

(3) Holding the same position, and without moving the head, look sharply to the right. In this position, raise and lower the eyebrows at a double time rate ten to twelve times.

(4) Holding the same position, without moving the head, look sharply to the left and raise and lower the eyebrows at a double-time rate ten to twelve times.

The Corrugator Supercilii Muscle

The corrugator supercilii is a short muscle that originates at the frontal bone above the rim of the eye at the inner corner. The muscle inserts into the skin at the arch of the eyebrow. When contracted, the corrugators pull the eyebrows together producing vertical wrinkles in the skin between the eyebrows. When the contraction of the corrugators is released, it is the job of the frontalis muscles to return the eyebrows to their natural spread apart position.

EXERCISE 8 - EYEBROWS DOWN AND OUT, LIFT AND SEPARATE

Purpose:

To eliminate vertical lines from between the eyebrows and remove the tension in the corrugated supercilii.

Exercise Steps (1) Put the first, second and third fingers equally spaced along the eyebrows. Press firmly enough to keep the eyebrows from pulling together.

(2) In the position of step 1, slowly pull the eyebrows down and slightly out to the sides against the resistance of the fingers. Do not allow the eyebrows to pull in toward the center of the face which will cause a vertical line to form between the brows. Pull down and out to a slow count of two.

(3) In the position of step 1, lift the eyebrows up and out to the sides to a slow count of two. Press hard enough to offer resistance so that your frontalis muscles are doing the lifting, not your fingers.

(4) With the eyebrows in the widely spaced position of step 1, repeat the pull down and out, lift and separate, working up to six times in all.

The Procerus Muscle

The procerus muscle originates from the lower part of the nasal bone and the lateral nasal cartilage. The fibers of the right and left procerus blend together at the top of the nose and insert into the skin of the lower forehead between the eyebrows. When contracted, the procerus muscles pull the inner corners of the eyebrows and the skin between the eyebrows down causing horizontal lines to form across the top of the nose. Releasing these wrinkles is the job of the central fibers of the frontalis but to do so, the procerus must relax or lengthen fully.

EXERCISE 9 - EYEBROWS DOWN TO NOSE AND STRETCH UP

Purpose:

To activate the fibers of the depressor supercilii and the procerus, building the tonus back into both muscle pairs so that they can resist the downward forces of gravity.

Preparation:

With the protective tape in place position the first and second fingers of each hand on the top of the cheeks. Press firmly so that the movement of the procerus and depresser supercilii can be isolated and keep the cheek muscles from moving as much as possible. In this position, wrinkle the nose slightly and pull the inner corners of the eyebrows straight down as far as they will go trying to pull them down to touch your nose. (Try to keep the cheek muscles out of this exercise as much as possible.) To do this, use the procerus and depresser supercilii muscles. Release the contraction by lifting the eyebrows back up.

Exercise Steps (1) Lower the inner corners of the eyebrows down to the nose and then raise the eyebrows straight up three times. On the third time raise the eyebrows as high as they will go.

(2) With the eyebrows raised fully, hold for a count of eight.

(3) Slowly lower the eyebrows to their normal position from the raised position to step two.

(4) Repeat steps 1, 2 and 3 four more times.

(5) Repeat the exercise using the forehead weight.

EXERCISE OF THE UPPER CHEEK MUSCLES

The Levator Labii Superioris Aleque Nasi

This muscle is lateral to the nose and runs parallel to it. It originates at the inner corner of the eye and runs downward and slightly laterally along the sides of the nose where it separates into two slips. The smaller slip terminates in the skin and cartilage of the nose. The larger slip terminates in the skin and muscle of the upper lip.

EXERCISE 17 - NOSE, WRINKLE-UPS

Purpose:

To fill in the hollows between the nose and the cheeks, to help prevent the nose from elongating and to keep the nostrils symmetrical.

Preliminary Preparation:

The forehead stiffener tape 10 under-eye tapes 12 with 12' and, optionally, the nose stiffener tapes 14 and 14' are applied as described. (Protective taping is to be used with all of the exercises.)

Exercise Steps (1) Place the fingers one hand firmly on the forehead and anchor them with the ball of the thumb. Doing this will isolate the action of the selected muscle and prevent the procerus muscle from getting involved.

(2) In this position, flare the nostrils and keep them flared, wrinkle up the nose as far as it will go to a maximum contraction. Be sure both sides of the nose are wrinkled evenly. The force of this contraction will draw the upper lip up.

(3) Release the contraction, concentrate on the upper lip and pull it forward toward the mirror and then down to meet the lower lip, closing your front teeth firmly together.

(4) With the mouth closed, inhale and exhale through the nose to relax.

(5) Repeat steps 1 through 4 four times.

The Levator Labii Superioris

This muscle originates from the maxilla, attaching to the bone under the lower center part of the eye, and extends downwardly and somewhat inwardly and inserts into the skin of the lateral half of the upper lip.

EXERCISE 17 - CHEEK ISOMETRICS

Purpose:

To lift and add contour to the upper cheek and to teach "facial posture".

Exercise Steps (1) Sit up tall and flare your nostrils and smile just slightly.

(2) Slowly lift the cheeks by contracting the cheek muscles. With the cheek muscles as tight as they will go, hold the contraction for a count of four.

(3) Allow the teeth to separate just a fraction of an inch and tighten the cheek muscles even further, pat/-pressing on the center of your cheek as you continue to squeeze in on those cheek muscles.

(4) Release the contraction in stages, bring the teeth back together, then bring the upper lip forward and down to meet the lower lip.

(5) With the lips and teeth firmly together, slowly release the tension in the cheek muscles to a count of four. With a closed mouth, inhale and exhale to relax.

(6) Repeat steps 1 through 5 three more times.

EXERCISE 18 - CHEEK LIFTS WITH WEIGHTS

Purpose:

In addition to improving tone and cheek muscles through isometrics, these repetitions with small cheek weights will develop strength and coordination.

Preparation:

Attach two cheek weights on the protective tape to each cheek one under the center of the eye down about one inch and the other slightly outward and upward from the first.

Exercise Steps (1) Pucker the lips and push them toward the mirror.

(2) In this position, contract the cheek muscles and raise the weights to a slow count of two.

(3) Release the contraction in the cheeks and lower the weights, again to a slow count of two. Be sure that the cheek muscles have released fully, by stretching the top lip (still in a pucker) toward the mirror.

(4) Repeat steps 1 through 3 nine more times.

(5) Pull the corners of the mouth out to the sides to make a broad "flat" smile. Keep the lips completely horizontal.

(6) Repeat steps 2 and 3 ten times.

The Zygomaticus Minor Muscle

This muscle originates from the lower portion of the cheek bone and travels obliquely downwardly and forwardly where it attaches to the upper lip just medial to the corner of the mouth.

EXERCISE 19 - SMILING WINKS

Purpose:

To improve the tonus condition of the outer two cheek muscles. This will lift the cheek up and in and diminish the naso-labial fold.

Exercise Steps (1) Sitting up straight and tall, raise the eyebrows and keep them raised throughout the exercise. Place three fingers from each hand on the outer forehead making sure that the pad of the little finger is right under the outer portion of the eyebrows. This isolates the movement of the zygomatics and keeps the other facial muscles from participating.

(2) Make a half smile with the right half of the mouth, pulling the right corners of the mouth out and up on a diagonal toward the middle of the ear.

(3) In this position, tighten both the right zygomaticus muscles and lift the cheek up and in hard as if trying to use the cheek to push the outer half of the lower eyelid closed. In other words, make a half of a wink.

(4) Release the cheek contraction but still keep the mouth in a "half smile". Repeat the wink, hold it and then release four times on the right side, each time trying to lift the cheek up and in higher toward the lower eyelid.

(5) Slowly relax the cheek muscles to a count of four. Pull the right corners of the mouth together and use them to push the right side of the mouth forward into a pucker position.

(6) Reverse the exercise and do it on the left side.

(7) Repeat steps 1 through 6 one time.

The Zygomaticus Major Muscle

This muscle originates at the outer part of the cheek bone and runs obliquely and terminates in the skin and mucosa at the corners of the mouth.

EXERCISE 21 - MOUTH CORNERS LIFT WITH HA-HA'S

Purpose: This isometric exercise tightens all of the muscles on the sides of the face. It will help to lift the cheeks and the corners of the mouth as well as the outer cheek area and help prevent or reduce the formation of jowls.

Exercise Steps (1) Open the mouth and make a great big smile, trying hard to lift the corners of the mouth as high as they will go.

(2) Hold the contraction of step 1 for a count of sixteen, trying to lift the corners of the mouth up higher and higher. Say "ha-ha" with the contracting and lifting to the count.

(3) Bring the lips forward and together to meet each other (be sure to bring the top lip down and the bottom lip up to meet each other in the middle).

(4) When the lips are together, slowly relax the cheek muscles to a slow count of two.

(5) Inhale and exhale to relax.

(6) Repeat steps 1 through 5 four more times.

CONCLUSION

Although the description of this invention has been given with reference to a particular embodiment, it is not to be construed in a limiting sense. Many variations and modifications will now occur to those skilled in the art. For a definition of the invention reference is made to the appended claims.

What is claimed is:

1. The method of exercising facial muscles for the purpose of tightening the skin comprising the steps of:
    selecting a muscle underlying the region of skin to be tightened,
    applying a primary stiffener by adhesion to the surface of the skin adjacent the selected muscle and applying secondary stiffeners by adhesion to other regions of skin which might be creased by contraction of the selected muscle,
    attaching a weight to the primary stiffener,
    and using the selected muscle repeatedly to lift and lower the weight in a controlled manner a predetermined number of times,
    whereby the selected muscle is shortened and the skin overlying it is tightened.

2. The invention as defined in claim 1 wherein the selected muscle is the occipitofrontalis and wherein the primary stiffener is applied to the skin of the forehead.

3. The invention as defined in claim 2 wherein the secondary stiffeners are applied under the eyes.

4. The invention as defined in claim 3 wherein the secondary stiffeners are applied on opposite sides of the top of the nose.

5. The invention as defined in claim 1 wherein the primary stiffener and the secondary stiffeners comprise adhesive tape.

6. The invention as defined in claim 1 wherein the weight is attached to the primary stiffener by a pressure sensitive adhesive on the weight.

7. The invention as defined in claim 1 wherein a primary stiffener is applied under each eye.

8. The invention as defined in claim 6 wherein the weight is wrapped with several layers of adhesive tape with the adhesive on the outside and including the step of removing, after the weight is removed, that portion of the adhesive tape which engaged the stiffener.

9. An exercise weight for use in exercising facial muscles comprising:
a plurality of metal disks disposed in a row,
a pair of thin flexible retaining plates disposed on opposite sides of said disks,
a wrapping of a plurality of layers of adhesive tape around said retaining plates, said adhesive tape having a pressure sensitive adhesive on the outer surface,
whereby said weight may be flexed to conform to the contour of a selected portion of a person's face and attached thereto by said tape and, after the weight is detached, the portion of the tape which was attached may be removed before the weight is attached again.

* * * * *